United States Patent [19]
Watanabe et al.

[11] Patent Number: 4,943,541
[45] Date of Patent: * Jul. 24, 1990

[54] GLASS CERAMICS

[75] Inventors: Akira Watanabe, Okayama; Yoshimitsu Takeuchi; Seiji Kihara, both of Bizen; Makoto Mitsudo, Okayama, all of Japan

[73] Assignee: Kyushu Refractories Co., Ltd., Okayama, Japan

[*] Notice: The portion of the term of this patent subsequent to Dec. 2, 2003 has been disclaimed.

[21] Appl. No.: 195,446

[22] Filed: May 13, 1988

Related U.S. Application Data

[63] Continuation of Ser. No. 893,571, Aug. 5, 1986, abandoned.

[30] Foreign Application Priority Data

Aug. 7, 1985 [JP] Japan ................. 60-174694

[51] Int. Cl.$^5$ ............................................ C03C 10/02
[52] U.S. Cl. ...................................... 501/10; 501/46; 501/48; 106/35
[58] Field of Search ................. 501/1, 10, 48, 46; 106/35

[56] References Cited

U.S. PATENT DOCUMENTS

| | | | |
|---|---|---|---|
| 3,253,934 | 5/1966 | Godron | 501/48 X |
| 3,519,445 | 7/1970 | MacDowell et al. | 501/100 R |
| 4,366,253 | 12/1982 | Yagi | 501/10 X |
| 4,417,912 | 11/1983 | Abe | 501/10 X |
| 4,626,514 | 12/1986 | Watanabe et al. | 501/48 X |

FOREIGN PATENT DOCUMENTS 1056111 3/1986 Japan .
1072653 4/1986 Japan .

OTHER PUBLICATIONS

McMillan, *Glass Ceramics*, 1969, pp. 79–80.

*Primary Examiner*—William R. Dixon, Jr.
*Assistant Examiner*—Karl Group
*Attorney, Agent, or Firm*—Koda and Androlia

[57] ABSTRACT

Glass ceramics used as dental material, artifical bone, etc. which contain 0.01 to 25 parts by weight of alkali metal oxides ($R_2O$), such as $Li_2O$, $Na_2O$, $K_2O$, $Rb_2O$, and $Cs_2O$, in 100 parts by weight of $CaO$-$Al_2O_3$-$P_2O_5$ system material. During the casting for obtaining the glass ceramics, the molten fluid is sufficiently distributed to the fine corners of a mold, and the temperature for crystallization is low. Also, the time required for the crystallization is short and the crystalline formed shows no internal defects, and has high bending strength.

2 Claims, No Drawings

GLASS CERAMICS

BACKGROUND OF THE INVENTION

1. Field of the Invention

The present invention relates to glass ceramics, and more particularly to an improvement of $CaO-Al_2O_3-P_2O_5$ system glass ceramics which are used as medical materials, which contain calcium phosphate crystals and are suitable as dental material, artifical bone, etc.

2. Prior Art

In recent years, ceramics are expanding their field of application tremendously, and are now even being used in the medical field. Also being attempted is the application of ceramics to medical materials, such as artificial dental material, for which metals and plastics have been conventionally used.

The inventors of this invention have conducted studies in order to find a ceramic material having an affinity for the living body and to establish a method to manufacture high strength ceramics in any preferred shape with high precision. As a result, it was found that the foregoing objects can be accomplished by using a calcium phosphate system material as the raw material.

Such calcium phosphate system material has several outstanding characteristics, but also has the following disadvantages such as when it is vitrified and crystallized internal defects are caused by the differences in specific gravity between glass and crystals, resulting in lowering the mechanical strength of the ceramic material. This, in turn, causes another problem in that bacteria can then enter the crystal through these defects.

For example, the specific gravity of calcium phosphate glass, which has calcium to phosphorus atomic ratio Ca/P of 0.48, is 2.63. When it is crystallized by heat treatment, and $CaO \cdot P_2O_5$ is produced. The true specific gravity of this $CaO \cdot P_2O_5$ crystal is 2.85, which is considerably higher than the specific gravity of the glass; however, because crystallization proceeds with a surface crystallization mechanism, almost no volumetric decrease occurs after crystallization occurs. An increase in specific gravity by crystallization means the volume to be decreased, and if the total volume is not changed, voids corresponding to the increase in specific gravity are formed inside of the crystal. These voids tend to bring about internal defects, such as cracks and pores. When these internal defects occur, the strength of the glass ceramics is lowered in comparison with that having no defects. Furthermore, since the size of pores formed and their distribution varies depending on various factors such as the atomic ratio of calcium to phosphorus of the glass, the crystallization temperature, the duration of crystallization, etc., it is inevitable that the mechanical strength of the glass ceramics also varies widely.

Likewise, these internal defects also occur in glass ceramics crystallized by a bulk crystallization mechanism although the extent of internal defects is somewhat lower, since some extent of volumetric shrinkage in bulk crystallization occurs.

The abovementioned problems can be solved if the difference in specific gravity before and after crystallization is eliminated. The inventors of this invention have sought in various ways for a method to prevent internal defects while maintaining the characteristic features of calcium phosphate that is an excellent affinity for the living body and a good cavitability, intact.

The inventors succeeded in solving the problems mentioned above by employing a $CaO-Al_2O_3-P_2O_5$ three component glass ceramics (Japanese Patent Provisional Publication No. 1986-186247).

That is, the crystals, which are formed when the glass of the $CaO-Al_2O_3-P_2O_5$ three component system are crystallized, are predominantly $CaO \cdot P_2O_5$, $2CaO \cdot P_2O_5$, and $Al_2O_3 \cdot P_2O_5$. The true specific gravity of each of these components is 2.85, 3.09, 2.59, respectively, and the specific gravity of $Al_2O_3 \cdot P_2O_5$ is comparatively lower than the other two types of calciuum phosphate crystals. For example, the specific gravity of a glass composed of 21.8 weight % of CaO, 9.3 weight % of $Al_2O_3$, and 68.9 weight % of $P_2O_5$ is 2.64. When this glass is crystallized, if the crystals formed consist of the abovementioned two types of calcium phosphates alone, the specific gravity of those crystals is higher than that of the glass. As a result, volumetric shrinkage is caused resulting in distortion of the external form, or, if volumetric shrinkage is not caused, defects, such as pores, occur inside the crystals. However, this glass also contains $Al_2O_3$, therefore, $Al_2O_3 \cdot P_2O_5$ that is low in specific gravity is formed concurrently. If crystals of $Al_2O_3 \cdot P_2O_5$ are produced in a sufficient amount, their volumetric expansion makes up for the volumetric shrinkage caused by the crystallization of calcium phosphate. As a result, the specific gravity after crystallization becomes 2.65. Thus, there is almost no difference in the specific gravity, and internal defects are not formed.

However, as the amount of $Al_2O_3$ is increased in order to decrease the difference in specific gravity before and after crystallization, the viscosity of the molten fluid increases. As a result, particularly in casting a tooth crown having a complicated shape, the casting of the molten fluid to the edges of the mold becomes impossible, making it actually infeasible to perform casting.

Moreover, when the amount of $Al_2O_3$ is further increased, both the softening point of the glass and the crystallization temperature of calcium phosphate increase. Due to the above, cracks may be caused by thermal stress during crystallization. Or, if crystallization is carried out at a low crystallization temperature to prevent the formation of cracks, the crystals $Al_2O_3 \cdot P_2O_5$ which are supposed to offset the difference in specific gravity are not sufficiently formed. This in turn causes the problem of making it impossible to prevent the formation of voids and cracks due to the difference in specific gravity before and after crystallization.

SUMMARY OF THE INVENTION

The present invention solved the problems mentioned above by adding alkali metal oxides (hereafter, referred to as $R_2O$; wherein R represents Li, Na, K, Rb, and Cs) to the composition of the $CaO-Al_2O_3-P_2O_5$ three component system.

In other words, the present invention provides a $CaO-Al_2O_3-P_2O_5$ glass ceramic that is characterized in that it contains 0.01 to 25 parts by weight of alkaline oxide selected from the group of $Li_2O$, $Na_2O$, $K_2O$, $Rb_2O$ and $Cs_2O$, in 100 parts by weight of $CaO-Al_2O_3-P_2O_5$ system material which is composed of 10 to 60 weight % of CaO, 5 to 25 weight % of $Al_2O_3$ and 25 to 85 weight % of $P_2O_5$.

As mentioned above, in the $CaO-Al_2O_3-P_2O_5$ three component system, due to the presence of $Al_2O_3$ the viscosity of the molten fluid is increased during casting, thereby making it impossible to sufficiently carry out casting. When $R_2O$ is added, the viscosity of the molten fluid can be lowered, and it becomes feasible to fully perform complicated casting even for a complex shape.

Further, the addition of $R_2O$ lowers the temperature for the crystallization of the $CaO-Al_2O_3-P_2O_5$ three component system, which is higher than the crystallization temperature for a $CaO-P_2O_5$ binary system, and thereby increase the rate of crystallization. These effects not only provide economical advantages, but also contribute to the prevention of deformation of the material by softening prior to crystallization, because if the crystallization temperature is lowered, it is possible to crystallize the cast glass while it is in the mold as it is. In addition, an increase in the crystallization rate cuts down duration of crystallization, and thereby also prevents deformation of the material by softening.

DETAILED DESCRIPTION OF THE INVENTION

The starting materials used in this invention are calcium-containing compounds which produce CaO by calcination, such as calcium oxide, calcium hydroxide, calcium carbonate or calcium oxalate; phosphorus-containing compounds which provide oxides of phosphorus through calcination, such as phosphoric acid and polyphosphoric acid; and aluminium containing compounds which become aluminium oxides by calcination, such as alumina and aluminium hydroxide. Also, calcium phosphate, apatite, aluminium phosphate, calcium aluminate, etc. may be used. For $R_2O$, besides oxide of alkali metal compounds such as hydroxide, carbonate, nitrate, etc. which produce oxide by calcination can be utilized.

One type or not less than two types of the compounds which contain calcium, phosphorus, aluminium, and an alkali metal, respectively, are first selected. Then, these raw materials are weighed so that the composition of the glass becomes 10 to 60 weight % for CaO, 5 to 25 weight % for $Al_2O_3$, 25 to 85 weight % for $P_2O_5$, so that the composition of $R_2O$ becomes 0.01 to 25 parts by weight to 100 parts by weight of the total amount of CaO, $Al_2O_3$ and $P_2O_5$.

When CaO is present in an amount of 60 weight % or above, or $P_2O_5$ is present in an amount less than 85 weight %, the melting temperature is elevated and vitrification cannot be achieved. On the contrary, when CaO is present in an amount less than 10 weight %, or $P_2O_5$ is present in an amount of 85 weight % or above, the melting temperature is lowered, and at the same time vitrification is easily achieved; however, crystallization treatment becomes difficult, and also chemical instability is invited due to the liberation of an excessive amount of phosphoric acid. On the other hand, when the content of alumina exceeds 25 weight %, the melting temperature is elevated, and when it is less than 5 weight %, the crystals of $Al_2O_3$ $P_2O_5$ are not formed or the amount formed is small, making it impossible to prevent internal defects, including pores. Thus, such cases are not desirable either.

Furthermore, depending on the types of the elements, alkali metal oxides differ in the effects of their activities. The effect of the activity of $Li_2O$ is the highest in degree, then, the effect becomes less in the order of $Na_2O$, $K_2O$, $Rb_2O$, and $Cs_2O$. Therefore, it is necessary to increase the amount of alkali metal oxides to be added, in the above order. The preferable amount to be added is 0.01 to 5 parts by weight for $Li_2O$, 0.02 to 10 weight for $Na_2O$, 0.03 to 15 parts by weight for $K_2O$, 0.04 to 20 parts by weight for $Rb_2O$, and 0.05 to 25 weight parts for $Cs_2O$, respectively, against 100 parts by weight of the total amount of CaO, $Al_2O_3$ and $P_2O_5$. When $R_2O$ is 25 parts by weight or above, the crystallized glass becomes unstable. For $R_2O$, it is also possible to use $Na_2O$, $K_2O$, $Rb_2O$ and $Cs_2O$ by mixing them appropriately.

The calcium phosphate system glass according to the present invention is basically composed of the three components, which are Ca, Al and P. When the glass ceramics obtained by the method of this invention is used as the material for a tooth crown, coloring agents may be added to give color and luster like that of natural teeth. In this case, one type or not less than two types of coloring agents selected from oxides of Zn, Fe, Mn, W, Ce, Ti, Ni, Co, Cr and V, are used. It is particularly preferable to use two or more types of oxides in combination. The amount to be added is set to be 0.01 to 15 parts by weight compared to 100 parts by weight of the $CaO-Al_2O_3-P_2O_5$ three component system oxides.

The raw materials are mixed thoroughly after weighing, then, the mixture is placed in a container, and melted at 900° C. or above, preferably to the range of 1000° to 1700° C. In this case, care should be taken because if the temperature for melting becomes 1800° C. or above, the phosphorus component becomes evaporated conspicuously.

After the melting, the mixture is cooled and vitrified. Then, the mixture is melted again and cast. The casting may be performed directly without cooling the molten raw material. For the $CaO-Al_2O_3-P_2O_5$ three component system material, since it is to be processed with the precision cast-molding, it is suitable to use the lost wax process which is used in casting the metal for dental use. The preheating temperature for the casting mold is 800° C. or below, preferably 200° to 800° C., and this preheating temperature is selected appropriately in accordance with the quality of casting mold material or of embedding material, the composition fo the glass to be cast, the temperature of the molten glass, etc.

The cast thus obtained is vitreous. Through converting this vitreous material into glass ceramics by heat treating, its characteristics can be improved remarkably. The method for the crystallization of the three component system glass ceramics of this invention is as described blow. That is, the molded material formed by the lost wax casting process is usually heated while remaining in the embedding mold, in an appropriate heating device, such as the electric furnace. The heating temperature in this case is below the melting point, preferably 500° to 900° C., and it is selected suitably depending on the composition of the glass.

EMBODIMENTS

Embodiments 1-5

Calcium carbonate powder, alumina powder, orthophosphoric acid and alkali metal carbonate were weighed with the arrangement to obtain the glass composition as shown in Table 1. After kneading them well, the mixture was melted at 1400° C. in a platinum crucible for one hour and cast in a mold of pressure casting apparatus wherein connective crown are embedded. Thereafter, the casting was cooled and vitrified. The glass thus obtained was held at 580° C. in the electric furnace for five hours and crystallized while being kept in the embedding mold.

Comparison Embodiment was prepared through melting, casting and crystallizing in exactly the same way as in the above Embodiments, except that alkali metal carbonate was not contained in the raw material.

TABLE I

| | EMBODIMENTS | | | | | COMPARISON EMBODIMENT |
|---|---|---|---|---|---|---|
| | 1 | 2 | 3 | 4 | 5 | 1 |
| Type of Alkali Metal | Li | Na | K | Rb | Cs | None |
| Composition (wt. pts.) | | | | | | |
| CaO | 21.8 | 21.8 | 21.8 | 21.8 | 21.8 | 21.8 |
| $Al_2O_3$ | 9.3 | 9.3 | 9.3 | 9.3 | 9.3 | 9.3 |
| $P_2O_5$ | 68.9 | 68.9 | 68.9 | 68.9 | 68.9 | 68.9 |
| $R_2O$ | 1.3 | 2.8 | 4.5 | 10.2 | 16.9 | — |
| Specific Gravity | | | | | | |
| Glass | 2.64 | 2.65 | 2.65 | 2.74 | 2.78 | 2.64 |
| Crystalline | 2.67 | 2.68 | 2.68 | 2.77 | 2.81 | 2.67 |
| Bending Strength after heat Treatment at 580° C. for 5 hours ($kg/cm^2$) | 1900 | 1800 | 1800 | 1700 | 1700 | 750 |

The glass obtained in each of the embodiments showed the complete casting in the mold without exception. After the crystallization, the glass was white and translucent, and as shown in Table 1, its three point bending strength was quite high. The X-ray diffraction revealed that $CaO \cdot P_2O_5$ and $Al_2O_3 \cdot P_2O_5$ were contained in the crystalline. Also, the difference in specific gravity between the glass and the crystalline was small in every case. When the microstructure of the crystalline was checked microscopically, the internal defects, such as pores were not observed.

The glass ceramics obtained in the embodiment for comparison was also white and translucent. However, the distribution of the molten fluid to the edges of the mold during the casting was not sufficient. Furthermore, under the same crystallization conditions as those for the embodiments of the invention, the temperature for the crystallization was so low that the crystallization was not carried out completely. As a result, the three point bending strength was 750 $kg/cm^2$ which was substantially lower than that of the embodiments.

Embodiments 6 and 7

By using the same method as in Embodiment 1, the glass ceramics of the $R_2O$ mixed systems shown in Table 2 were prepared.

The glass ceramics obtained were similar to those obtained in the Embodiments 1 through 5, and because of the addition of $R_2O$, the casting formability and the bending strength were both satisfactory.

TABLE 2

| COMPOSITION (wt. pts.) | EMBODIMENT 6 | EMBODIMENT 7 |
|---|---|---|
| CaO | 21.8 | 21.8 |
| $Al_2O_3$ | 9.3 | 9.3 |
| $P_2O_5$ | 68.9 | 68.9 |
| $Li_2O$ | 0.7 | 0.6 |
| $Na_2O$ | 1.4 | 0.7 |
| $K_2O$ | — | 1.2 |
| Specific Gravity | | |
| Glass | 2.65 | 2.64 |
| Crystalline | 2.68 | 2.67 |
| Bending Strength after Heat Treatment at 580° C. for 5 hours ($kg/cm^2$) | 1850 | 1800 |

As should be apparent from the embodiments, the material in which $R_2O$ is added in the $CaO$—$Al_2O_3$—$P_2O_5$ system glass ceramics, that is provided by the present invention, shows satisfactory distribution of the molten fluid to every corner of the embedding mold during the casting. Also, when compared with the samples which contain no $R_2O$, the material of this invention is lower in the temperature for crystallization, and the time for crystallization is shorter. In addition, in the present invention, the difference in specific gravity between the glass and the crystalline is small, no internal defects are observed in the crystals, and higher bending strength than that of the sample which does not contain $R_2O$ is obtained when the crystallization temperature is low.

We claim:

1. A $CaO$—$Al_2O_3$—$P_2O_5$ glass ceramics consisting essentially of 0.01 to 25 parts by weight of alkaline oxides selected from the group consisting of $Li_2O$, $Rb_2O$, and $Cs_2O$, in a 100 parts by weight of the crystalline glass composed of 10 to 60 weight % of CaO, 5 to 25 weight % of $Al_2O_3$, and 25 to 85 weight % of $P_2O_5$.

2. A $CaO$—$Al_2O_3$—$P_2O_5$ glass ceramic consisting essentially of 0.01 to 25 parts by weight of alkaline oxides selected from the group consisting of $Li_2O$, $Rb_2O$ and $Cs_2O$, in a 100 parts by weight of crystalline glass consisting of 10 to 60 parts by weight of CaO, 5 to 25 parts by weight of $Al_2O_3$ and 25 to 85 parts by weight of $P_2O_5$ and 0.01 to 15 parts by weight of a coloring agent compared to 100 parts by weight of $CaO$—$Al_2O_3$—$P_2O_5$ crystalline glass, said coloring agent selected from the group consisting of two or more oxides of Zn, Fe, Mn, W, Ce, Ti, Ni, Co, Cr and V.

* * * * *